United States Patent [19]

Mori

[11] Patent Number: 4,989,931
[45] Date of Patent: Feb. 5, 1991

[54] SOLAR-RAY ENERGY RADIATION DEVICE FOR MEDICAL APPLICATION

[76] Inventor: Kei Mori, 3-16-3-501, Kaminoge, Setagaya-ku, Tokyo, Japan

[21] Appl. No.: 937,654

[22] Filed: Dec. 4, 1986

[30] Foreign Application Priority Data

Jan. 9, 1986 [JP] Japan .................................... 61-2662

[51] Int. Cl.$^5$ .......................... G02B 6/00; G02B 27/00
[52] U.S. Cl. .................................. 350/96.10; 128/395
[58] Field of Search ........................... 350/96.10, 96.29; 128/303.1, 362, 305, 398

[56] References Cited

U.S. PATENT DOCUMENTS

| | | | |
|---|---|---|---|
| 1,137,393 | 4/1915 | Fogg | 128/395 |
| 1,746,893 | 2/1930 | Homan | 128/395 |
| 4,556,875 | 12/1985 | Ishiwatari | 128/303.1 |

Primary Examiner—John Zazworsky
Attorney, Agent, or Firm—Jordan and Hamburg

[57] ABSTRACT

A solar-ray energy radiation device for medical application comprises a transparent or semi-transparent cylindrical member, a cover-member for closing off one end of the cylindrical member, and an optical conductor cable having a light-ray emitting end disposed at approximately the central portion of the cover-member. The solar-ray energy transmitted through the optical conductor cable is emitted from the light-ray emitting end into the cylindrical member. An open-ended side of the cylindrical member is placed in such a way as to emit solar-ray energy onto a place needing medical treatment. The cylindrical member has notches or holes causing the inner and outer portions of the cylindrical member to come in contact with each other at the open-ended side wall.

7 Claims, 1 Drawing Sheet

SOLAR-RAY ENERGY RADIATION DEVICE FOR MEDICAL APPLICATION

BACKGROUND OF THE INVENTION

The present invention relates to a solar-ray energy radiation device for medical application, in particular, a light-ray radiation device used for medical treatment and which radiates light-ray energy corresponding to the visible light-ray component of solar-rays onto a diseased part or a desired portion of a patient as a form of medical treatment; or radiates the same onto the surface of a person's skin as a beauty treatment or for the promotion of health.

In recent years, a large number of persons suffer from incurable diseases such as arthritis, neuralgia and rheumatism, or from pain caused by injury, a bone fracture or a pain from an unknown disease. Furthermore, persons cannot avoid having their skin show signs of aging which progresses gradually from a comparatively young age. On the other hand, the present application has previously proposed to focus solar-rays or artificial light-rays by the use of lenses or the like, and to guide the same into an optical conductor, then to transmit them onto an optional desired place through the optical conductor. Those light-rays transmitted in such a way are employed for use in illumination or for the like purposes, as for example, to cultivate plants, chlorella, and the like. In such a process, visible light-rays not containing ultraviolet infrared rays promote health and thereby prevent a person's skin from the appearance of aging. Furthermore, the effects of those visible light-ray are very noticeable in giving patients relief from arthritis, neuralgia, bedsores, rheumatism, injuries scars, bone fractures and the like, as well as for stopping pain resulting therefrom. Such results have been corroborated by the present applicant's own experience.

SUMMARY OF THE INVENTION

IT is an object of the present invention to provide a light-ray radiation device for medical application in the treatment of various medical problems for administering beauty treatments, or for promoting health.

It is another object of the present invention to provide a light-rays radiation device for effectively emitting light-ray corresponding to the visible light-ray components of solar-rays that do not contain harmful rays such as ultraviolet or infrared.

It is another object of the present invention to provide a solar-ray energy radiation device for medical application comprising a transparent or semi-transparent cylindrical member, a cover-member for closing off one end of the cylindrical member, and an optical conductor cable having a light-ray emitting end disposed at approximately the central portion of the cover-member, in which solar-ray energy transmitted through the optical conductor cable is emitted from the end of the light-ray emitting end thereof into the cylindrical member, and an open-ended side of the cylindrical member is placed in such a way as to emit solar-ray energy onto a place needing medical treatment.

It is another object of the present invention to provide a solar-ray energy radiation device comprising a transparent or semi-transparent cylindrical member having notches or holes at the open-ended side wall to prevent the interior of the cylindrical member from becoming fogged up.

It is another object of the present invention to provide a solar-ray energy radiation device comprising a transparent or semi-transparent cylindrical member formed in a shape suitable for accommodating a light-ray radiating portion at the open-ended side thereof to radiate solar-ray energy effectively onto the irregular skin surface of person without causing the solar-ray energy to leak outside of the device.

It is another object of the present invention to provide a solar-ray energy radiation device having a timer and an alarm signaling device for informing the user when the time period of its use has finished.

The above-mentioned features and other advantages of the present invention will be apparent from the following detailed description which goes with the accompanying drawings.

DESCRIPTION OF THE PREFERRED EMBODIMENTS

Figure 1:
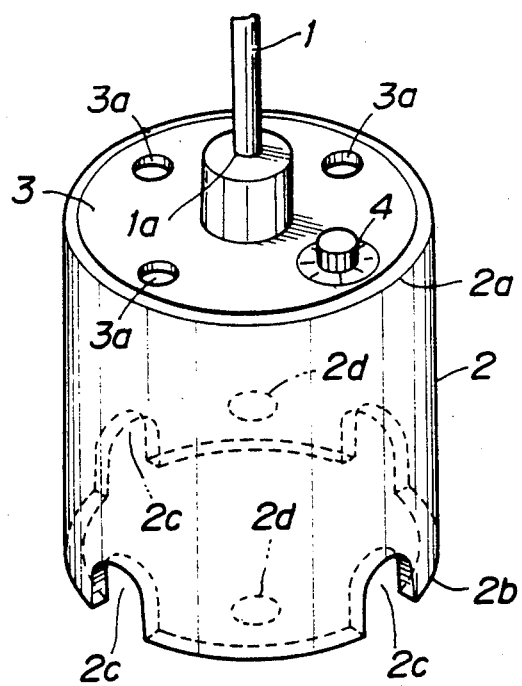
FIGS. 1 and 2 are, respectively, perspective views for explaining two embodiments of a solar-ray energy radiation device according to the present invention.

FIG. 1 is a perspective view for explaining an embodiment of a light-ray radiation device for medical application according to the present invention. In FIG. 1, 1 is an optical conductor cable. Solar-rays or artificial light-rays are guided into the optical conductor cable 1 from the end portion thereof and transmitted therethrough. The light-ray (the white-colored light-rays), corresponding to the visible light-ray components of solar-rays, are transmitted through an optical conductor cable 1 in such a manner as was previously proposed in various ways by the present applicant. 2 is a semi-transparent or transparent cylindrical member attached to the optical conductor cable 1 at the light-rays emitting portion side 1a thereof, and 3 is a cover member for closing one end side 2a of the cylindrical member 2. The light-ray emitting end side 1a of the optical conductor cable 1 is placed at approximately the central portion of the cover member 3. Solar-ray energy transmitted through the optical conductor cable 1 is channeled into the cylindrical member 2.

At the time of its use for medical treatment, another end 2b of the cylindrical member 2 is brought in line with the position for medical treatment or placed opposite the same keeping at a desired distance. The light-ray, consisting of visible light-ray components transmitted through the optical conductor cable 1, as mentioned before, are focused onto a diseased part, a desired portion of a patient, or other various parts of the human body. As mentioned above, the light-rays to be radiated onto a diseased part of a patient are light-rays corresponding to the visible light-ray components of solar-rays and do not contain ultraviolet or infrared rays. Thereby, it will be possible to administer medical treatment without the patient suffering from the harmful effects of ultraviolet or infrared rays.

According to the present invention, since the cylindrical body 2 will be made of a semi-transparent or transparent substance, the position of the light-rays and their approximate intensity can be monitored by observing them with the naked eye. However, in the case for bringing the end portion 2b of the cylindrical member 2 into tight contact with a diseased part or a desired portion of a patient, there is a fear that the inner wall of the cylindrical member 2 will become fogged up by the vapors of sweat discharged from the surface of human skin, and thereby the interior of the cylindrical member 2 could not be seen from the outside.

The present invention was made for the purpose of solving such an inconvenience. In the case of the embodiment shown in FIG. 1, notches 2c are formed at the end portion 2b of the cylindrical member 2 or through-holes 2d are formed on the side wall of the cylindrical member 2 so as to pass air therethrough, and further, through-holes 3a are formed on the cover member 3. In such a construction, air can flow freely inside the cylindrical member 2, and therefore it will be possible to prevent the interior of the cylindrical member 2 from becoming fogged up and of consequently being filled with moisture.

Furthermore, in the case of medical applications by emitting solar-ray energy onto a diseased part or a desired portion of a patient as mentioned above, the time period for light-ray application will differ in accordance with the condition of the diseased part. It is troublesome to keep watch on the timing of the radiation treatment. A timer 4 is employed for monitoring the above-mentioned radiation time period. The time period to be set is recorded on a card, or the like not shown in FIG. 1. For example, it is recorded thereon in every application of the diseased condition. By referring to the card, the patient establishes the radiation time period. When the timer 4 measures (counts) the treatment time, it sends out an alarm sound or turns on a lamp to inform the patient that the time has finished.

Figure 2:
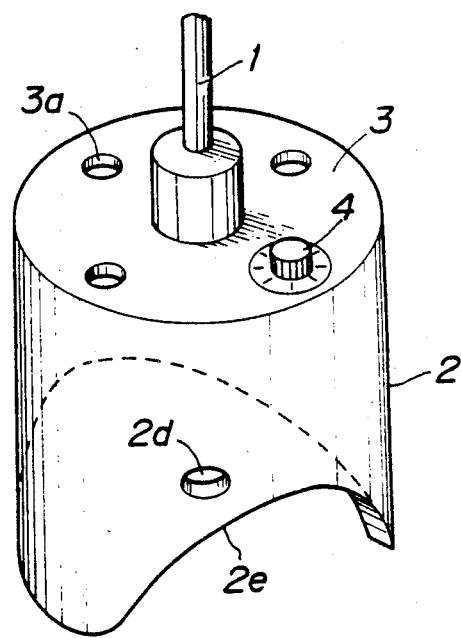

FIG. 2 is a construction view for explaining another embodiment of a solar-ray energy radiating device according to the present invention. In this embodiment, the end portion 2b of the cylindrical member 2 is formed in a shape 2e corresponding to that of the limited portion upon which solar-ray energy is radiated. In the case of the embodiment shown in FIG. 2, the shape 2e is so formed that the diameter thereof coincides with that of the arm or the leg of a person. Thereby, it will be possible to radiate solar-ray energy effectively onto the irregular skin surface of a person, namely, to radiate the same onto a diseased part of such a skin surface without causing the solar-ray energy to leak outside of the device. Moreover, in FIG. 2, the part performing the same action as that in the embodiment shown in FIG. 1 is represented by the same reference numeral as that of FIG. 1.

As is apparent from the foregoing description, according to the present invention, it may be possible to provide a solar-ray energy radiation device for medical application. After making sure of the position of the light-ray radiation and the approximate light-ray intensity by observing both of them with the naked eye, solar-ray energy can be effectively radiated onto a diseased part or a desired portion of a patient's body and further, there is no fear that those applications cannot be performed at half-strength of the radiation, and the light-ray can be emitted for a controlled period of time.

I claim:

1. A solar-ray energy radiation device for the application of the visible light rays component of solar rays to a localized part of a person's body comprising a cylindrical means having a cylindrical portion with a longitudinal axis and a closure portion on one longitudinal end of said cylindrical portion, said cylindrical portion being made of a transparent or a semi-transparent material, an optical conductor for transmitting the visible light rays component of solar rays from which ultraviolet rays and infrared rays have been excluded, said optical conductor having a light-rays emitting end mounted on said closure portion at a position generally aligned with the axis of said cylindrical portion such that the visible light-rays component of solar rays emitted from said light-rays emitting end of said optical conductor pass into said cylindrical portion, the other longitudinal end of said cylindrical portion operable to contact a person's body such that a part of said person's body is encircled by said contact means, and opening means in said cylindrical means to permit air to pass between the interior and exterior of said cylindrical means, whereby the visible light-rays component of solar rays pass from said light-emitting end through the interior of said cylindrical portion to said encircled part of said person's body while said opening means precludes fogging and moisture build-up within said cylindrical means during application of the device on a person's body.

2. A solar-ray energy radiation device according to claim 1 wherein said other end of said cylindrical portion is defined by an end face, said contact means comprising two generally U-shaped indentations in said end face, each of said two U-shaped indentations being diametrically opposed to one another so as to receive a person's limb during application of the device to a person's body.

3. A solar-ray energy radiation device according to claim 1 further comprising a timer-alarm means on said cylindrical means for timing the application of said solar-rays to said encircled part of said person's body and for indicating an alarm after a preset amount of time has elapsed.

4. A solar-ray energy radiation device according to claim 3 wherein said timer-alarm means is disposed on said closure portion.

5. A solar-ray energy radiation device according to claim 1 wherein said opening means comprises openings in said closure portion.

6. A solar-ray energy radiation device according to claim 1 wherein said opening means comprises openings in said cylindrical portion.

7. A solar-ray energy radiation device for the application of the visible light rays component of solar rays to a localized part of a person's body comprising a cylindrical means having a cylindrical portion with a longitudinal axis and a closure portion on one longitudinal end of said cylindrical portion, said cylindrical portion being made of a transparent or a semi-transparent material, an optical conductor for transmitting the visible light rays component of solar rays from which ultraviolet rays and infrared rays have been excluded, said optical conductor having a light-rays emitting end mounted on said closure portion at a position generally aligned with the axis of said cylindrical portion such that the visible light rays component of solar rays emitted from said light-rays emitting end of said optical conductor pass into said cylindrical portion, the other longitudinal end of said cylindrical portion being open, contact means on said open end of said cylindrical portion operable to contact a person's body such that a part of said person's body is encircled by said contact means, said contact means comprising two generally U-shaped indentations in the other longitudinally end of said cylindrical portion, each of said two U-shaped indentations being diametrically opposed so as to receive a person's limb during application of the device to a person's body, a timer-alarm means on said cylindrical means for timing the application of said visible light rays component of solar rays to said encircled part of said person's body and for indicating an alarm after a preset amount of time has elapsed, and opening means in said cylindrical means to permit air to pass between the interior and exterior of said cylindrical means, whereby the visible light-rays component of light rays pass from said light-emitting end through the interior of said cylindrical portion to said encircled part of said person's body while said opening means precludes fogging and moisture build-up with said cylindrical means during application of the device to a person's body.

* * * * *